US011096392B2

(12) United States Patent
Hurst et al.

(10) Patent No.: US 11,096,392 B2
(45) Date of Patent: Aug. 24, 2021

(54) BACTERIA AND USES THEREOF

(71) Applicant: AgResearch Limited, Hamilton (NZ)

(72) Inventors: Mark Robin Holmes Hurst, Christchurch (NZ); Travis Robert Glare, Christchurch (NZ)

(73) Assignee: AgResearch Limited, Hamilton (NZ)

( * ) Notice: Subject to any disclaimer, the term of this patent is extended or adjusted under 35 U.S.C. 154(b) by 0 days.

(21) Appl. No.: 16/054,952

(22) Filed: Aug. 3, 2018

(65) Prior Publication Data

US 2018/0332858 A1    Nov. 22, 2018

Related U.S. Application Data

(62) Division of application No. 14/791,107, filed on Jul. 2, 2015, now Pat. No. 10,039,286, which is a division of application No. 12/303,872, filed as application No. PCT/NZ2007/000146 on Jun. 8, 2007, now abandoned.

(30) Foreign Application Priority Data

Jun. 8, 2006 (AU) .............................. 2006903111

(51) Int. Cl.
*A01N 63/00* (2020.01)
*C12N 1/20* (2006.01)
*C12R 1/01* (2006.01)
*A01N 63/20* (2020.01)

(52) U.S. Cl.
CPC ............. *A01N 63/00* (2013.01); *A01N 63/20* (2020.01); *C12N 1/20* (2013.01); *C12R 1/01* (2013.01)

(58) Field of Classification Search
None
See application file for complete search history.

(56) References Cited

U.S. PATENT DOCUMENTS

| 7,244,607 | B2 | 7/2007 | Martin et al. |
| 8,020,343 | B2 | 9/2011 | Pearce et al. |

FOREIGN PATENT DOCUMENTS

| WO | WO 2005/073726 | 8/2005 |
| WO | WO 2008/041863 A1 | 4/2008 |

OTHER PUBLICATIONS

Ffrench-Constant, et al., "An ABC guide to the bacterial toxin complexes", Adv. Appl. Microbiol., 2006; 58: 169-83.
Bauce, et al., "*Bacillus thuringiensis* subsp, *kurstaki* Aerial Spray Prescription for Balsam Fir Stand Protection Against Spruce Budworm (Lepidoptera: Tortricidae)" *J. of Economic Entomology* (Oct. 2004) 97(5): 1624-1634.
Bercovier, et al., "Genus XIV. *Yersinia* Van Loghem 1944, 15[AL]" in *Bergey's Manual of Systematic Bacteriology*, vol. 1, Krieg, N. R. & J.G. Holt (Eds.), Williams & Wilkins, Baltimore (1984) 498-506.
Bresolin, et al., "Low temperature-induced insecticidal activity of *Yersinia enterocoliticia*" *Molecular Microbiology* (2006) 59(2): 503-512.
Burges, et al., "Formulation of Bacteria, Viruses and Protozoa to Control Insects" in *Formulation of Microbial Biopesticides: microorganisms, nematodes and seed tretments*, H.D. Burges (Ed.), Kluwer Academic Publishers, Dordrecht (1998) 34-127.
Cashion, et al., "A Rapid Method for the Base Ratio Determination of Bacterial DNA" *Analytical Biochemistry* (1977) 81: 461-466.
Cathala, et al., "Laboratory Methods: A Method for Isolation of Intact, Translationally Active Ribonucleic Acid" *DNA* (1983) 2(4): 329-335.
Chiou, et al., "Formulation of *Bacillus amyloliquefaciens* B190 for Control of Lily Grey Mould (*Botrytis elliptica*)" *J. Phytopathology* (2003) 151: 13-18.
De Ley, et al., "The Quantitative Measurement of DNA Hybridization from Renaturation Rates" *Eur. J. Biochem.* (1970) 12: 133-142.
Erickson, et al., "Acute oral toxicity of *Yersinia pseuodtuberculosis* to fleas: implications for the evolution of vector-borne transmission of plague" *Cellular Microbiology* (2007) 9(11): 2658-2666.
Hofte, et al., "Insecticidal Crystal Proteins of *Bacillus thuringiensis*" *Microbiological Reviews* (Jun. 1989) 53(2): 242-255.
Huss, et al., "Studies on the Spectrophotometric Determination of DNA Hybridization from Renaturation Rates" *System. Appl. Microbiol.* (1983) 4: 184-192.
Ibrahim, et al., "A cluster of atypical *Yersinia* strains with a distinctive 16S rRNA signature" *FEMS Microbiology Letters* (1997) 146: 73-78.
Kado, et al., "Rapid Procedure for Detection and Isolation of Large and Small Plasmids" *J. of Bacteriology* (May 1981) 145(3): 1365-1373.
Kotetishvili, et al., "Multilocus Sequence Typing for Studying Genetic Relationships among *Yersinia* Species" *J. of Clinical Microbiology* (Jun. 2005) 43(6): 2674-2684.
Lindow, et al., "Temporal Dynamics of the Biocontrol Agent *Pseudomonas fluorescens* Strain A506 in Flowers in Inoculated Pear Trees" *Bacteriology* (2003) 93(6): 727-737.
Lysenko, O., "Non-Sporeforming Bacteria Pathogenic to Insects: Incidence and Mechanisms" *Ann. Rev. Microbiol.* (1985) 39: 673-695.
Maa, et al., "Biopharmaceutical Powders: Particle Formation and Formulation Considerations" *Current Pharmaceutical Biotechnology* (2000) 1: 283-302.
Mesbah, et al., "Precise Measurement of the G+C Content of Deoxyribonucleic Acid by High-Performance Liquid Chromatography" *International J. of Systematic Bacteriology* (Apr. 1989) 39(2): 159-167.

(Continued)

*Primary Examiner* — Michelle F. Paguio Frising
(74) *Attorney, Agent, or Firm* — Knobbe, Martens, Olson & Bear, LLP

(57) ABSTRACT

The present invention relates to a novel bacterium *Yersinia entomophaga* MH96 as deposited at DSMZ on 4 May 2006 and designated accession no. DSM 18238. The present invention also relates to substances obtained or derived from *Yersinia entomophaga* MH96, which retain biopesticide activity. Methods for protecting a plant from pest infestation which include applying to the plant or its environment an effective amount of *Yersinia entomophaga* MH96 or a product delivered from the bacterium are also described.

9 Claims, 11 Drawing Sheets

Specification includes a Sequence Listing.

(56) References Cited

OTHER PUBLICATIONS

O'Callaghan, et al., "Isolation and enumeration of *Serratia entomophila*—a bacterial pathogen of the New Zealand grass grub, *Costelytra zealandica*" *J. of Applied Bacteriology* (1993) 75: 307-314.

Pinheiro, et al., "Expression and insecticidal activity of *Yersinia pseudotuberculosis* and *Photohabdus luminescens* toxin complex proteins" *Cellular Microbiology* (2007) 9(10): 2372-2380.

Pitcher, et al., "Rapid extraction of bacterial genomic DNA with guanidium thiocyanate" *Letters in Applied Microbiology* (1989) 8: 151-156.

Saitou, et al., "The Neighbor-joining Method: A New Method for Reconstructing Phylogenetic Trees" *Mol. Biol. Evol.* (1987) 4(4): 406-425.

Teera-Arunsiri, et al., "Preparation of Spray-Dried Wettable Powder Formulations of *Bacillus thuringiensis*-Based Biopesticides" *J. of Economic Entomology* (Apr. 2003) 96(2): 292-299.

Tennant, et al., "Homologues of Insecticidal Toxin Complex Genes in *Yersinia enterocolitica* Biotype 1A and Their Contribution to Virulence" *Infection and Immunity* (Oct. 2005) 73(10): 6860-6867.

Wayne, et al., "Report of the Ad Hoc Committee on Reconciliation of Approaches to Bacterial Systematics" *International J. of Systematic Bacteriology* (Oct. 1987) 37(4): 463-464.

International Search Report issued in International Application No. PCT/NZ2007/000146, dated Nov. 13, 2007.

https://www.dsmz.de/catalogues/details/culture/DSM-22339.html, accessed Sep. 10, 2012.

http://www.uniprot.org/uniprot/B6A8B5, accessed Sep. 10, 2012.

http://www.ebi.ac.uk/ena/data/view/DQ400835.1, accessed Sep. 10, 2012.

Deposit certificate for Accession No. DSM 18328, deposited at Leibniz Institute DSMZ-German Collection of Microorganisms and Cell Cultures GmbH (DSMZ) on May 4, 2006.

Hurst, et al., "*Yersinia entomophaga* sp. nov., isolated from the New Zealand grass grub *Costelytra zealandica*", International Journal of Systematic and Evolutionary Microbiology (2011), 61, 844-849.

Landsberg, et al., "3D structure of the *Yersinia entomophaga* toxin complex and implications for insecticidal activity", PNAS, vol. 108, No. 51, pp. 20544-20549, Dec. 20, 2011.

BACTERIA AND USES THEREOF

RELATED APPLICATIONS

This application is a continuation of U.S. patent application Ser. No. 14/791,107, filed Jul. 2, 2015, now U.S. Pat. No. 10,039,286, which is a divisional of U.S. patent application Ser. No. 12/303,872, filed Mar. 1, 2010, now abandoned, which is a U.S. National Phase of International Application No. PCT/NZ2007/000146, filed Jun. 8, 2007, designating the U.S., which claims priority to Australian Patent Application Number 2006903111, filed Jun. 8, 2006, the entire contents of each of which are incorporated herein by reference.

REFERENCE TO SEQUENCE LISTING

The present application is being filed along with a Sequence Listing in electronic format. The Sequence Listing is provided as a file entitled JAMES132_002C1.TXT, created Aug. 2, 2018, which is 2,321 bytes in size. The information in the electronic format of the Sequence Listing is incorporated herein by reference in its entirety.

TECHNICAL FIELD

The present invention relates to a novel bacterium and uses thereof. In particular, the present invention relates to applications concerned with the biopesticide activity of the novel bacterium and of its mutant or variant strains. The present invention also concerns substances obtained or derived from the aforesaid bacteria.

BACKGROUND ART

The invention describes a pesticide strain of a new species to be called *Yersinia entomaphaga* that is active against a wide range of insect species. The novel bacterium also produces a toxic filtrate component that is also useful as a biopesticide agent in the control of insect species.

A novel insecticidal bacterium isolated from a New Zealand insect is described. The bacterium is a new species residing within the genus *Yersinia* and has been named *Yersinia entomophaga* MH96. *Y. entomophaga* has a broad host range towards members of the coleopteran and lepidopteran species amongst others. Death occurs within 72 hours post inoculation. The infection process appears to be due to a rapid build up in the bacterial population followed by a rapid invasion of the haemocoel leading to the cadaver taking on a deliquescing black appearance. Data are provided on biochemical utilisation tests (API), DNA sequences relating to phylogenetic analysis encompassing 16s ribosomal RNA sequencing and MLST sequence analysis of known *Yersinia* genes is given. In addition the DNA sequence of ~132 short random *Y. entomophaga* genomic sequences are given.

A gram-negative bacterium was isolated from an infected grass grub field collected from New Zealand soils. Inoculation of grass grub larvae with the bacterium showed that death occurred within 2-3 days at 15° C. Standard biochemical identification using API20E and API50CH test strips indicated the bacterium is a member of the Enterobacteriaceae most similar to *E. sakazakii*, but subsequent molecular characterisation placed it in the genus *Yersinia*.

The continued use of *B. thuringiensis* and derivatives as a biopesticide over many years can lead to an increase in resistant insects. There is, therefore, a need for novel biopesticides to control insects.

There is also a need for biological control agents such as biopesticides to provide an alternative to chemical pesticides which can be toxic to non-target organisms in the environment.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

It is an object of the present invention to address the foregoing problems or at least to provide the public with a useful choice.

Further aspects and advantages of the present invention will become apparent from the ensuing description which is given by way of example only.

DISCLOSURE OF INVENTION

The original organism name *Yersinia entomophagous* MH-1 has been amended herein to refer to *Yersinia entomophaga* MH96, to conform to the official nomenclature of this organism. Thus, it should be clear that both names refer to the same organism as originally described in the provisional specification and the subject of the biological deposit at DSMZ on 4 May 2006 and designated accession no. DSM 18238.

It should be appreciated by those skilled in the art that unless the context clearly relays otherwise use of the terms *Yersinia entomophaga* MH96 or bacteria in this specification should also be taken to include mutant and variant strains of *Yersinia entomophaga* MH96 which retain the biopesticide activity.

According to a first aspect of the present invention there is provided an isolated *Yersinia entomophaga* MH96 bacterium deposited at DSMZ on 4 May 2006 and designated accession no. DSM 18238.

According to a second aspect of the present invention there is provided the use of *Yersinia entomophaga* MH96 to directly or indirectly obtain a biopesticide.

According to a third aspect of the present invention there is provided the use of *Yersinia entomophaga* MH96 as a biopesticide.

According to a fourth aspect of the present invention there is provided the use of *Yersinia entomophaga* MH96 in the manufacture of a composition suitable as a biopesticide.

According to a fifth aspect of the present invention there is provided a culture of *Yersinia entomophaga* MH96 as deposited at DSMZ on 4 May 2006 and designated accession no. DSM 18238.

According to a sixth aspect of the present invention there is provided the use of a culture of *Yersinia entomophaga* MH96 to directly or indirectly obtain a biopesticide According to a seventh aspect of the present invention there is provided the use of a culture of *Yersinia entomophaga* MH96 as a biopesticide.

According to a eighth aspect of the present invention there is provided the use of a culture of *Yersinia entomophaga* MH96 in the manufacture of a composition suitable as a biopesticide.

According to a ninth aspect of the present invention there is provided a cellular extract obtained from *Yersinia entomophaga* MH96 as deposited at DSMZ on 4 May 2006 and designated accession no. DSM 18238 or a culture thereof.

According to a tenth aspect of the present invention there is provided the use of a cellular extract of *Yersinia entomophaga* MH96 to directly or indirectly obtain a biopesticide.

According to an eleventh aspect of the present invention there is provided the use of a cellular extract of *Yersinia entomophaga* MH96 as a biopesticide.

According to a twelfth aspect of the present invention there is provided the use of a cellular extract of *Yersinia entomophaga* MH96 in the manufacture of a composition suitable as a biopesticide.

According to a thirteenth aspect of the present invention there is provided a sonicated cell filtrate of *Yersinia entomophaga* MH96 as deposited at DSMZ on 4 May 2006 and designated accession no. DSM 18238 which has a biopesticide activity.

According to a fourteenth aspect of the present invention there is provided the use of a sonicated cell filtrate of *Yersinia entomophaga* MH96 to directly or indirectly obtain a biopesticide.

According to a fifteenth aspect of the present invention there is provided the use of a sonicated cell filtrate of *Yersinia entomophaga* MH96 as a biopesticide.

According to a sixteenth aspect of the present invention there is provided the use of a sonicated cell filtrate of *Yersinia entomophaga* MH96 in the manufacture of a composition suitable as a biopesticide.

According to a further aspect of the present invention there is provided a supernatant of a whole broth culture of *Yersinia entomophaga* MH96 as deposited at DSMZ on 4 May 2006 and designated accession no. DSM 18238.

According to a further aspect of the present invention there is provided the use of the supernatant of a whole broth culture of *Yersinia entomophaga* MH96 as a biopesticide.

According to a further aspect of the present invention there is provided the use of the supernatant of a whole broth culture of *Yersinia entomophaga* MH96 to directly or indirectly obtain a biopesticide.

According to a further aspect of the present invention there is provided the use of the supernatant of a whole broth culture of *Yersinia entomophaga* MH96 in the manufacture of a composition suitable as a biopesticide.

According to a further aspect of the present invention there is provided a composition that includes an effective amount of *Yersinia entomophaga* MH96 wherein said bacteria exhibits a biopesticide activity.

According to a further aspect of the present invention there is provided a composition formulated from an effective amount of a culture of *Yersinia entomophaga* MH96 wherein said culture exhibits a biopesticide activity.

According to a further aspect of the present invention there is provided a composition included an effective amount *Yersinia entomophaga* MH96, wherein *Yersinia entomophaga* MH96 has been killed as an intact form and maintains a biopesticide activity.

According to a further aspect of the present invention there is provided a composition formulated from an effective amount of a whole broth culture of *Yersinia entomophaga* MH96 wherein said whole broth culture exhibits a biopesticide activity.

According to a further aspect of the present invention there is provided a composition formulated from an effective amount of a supernatant of a whole broth culture of *Yersinia entomophaga* MH96 wherein the supernatant from the culture exhibits a biopesticide activity.

According to a further aspect of the present invention there is provided a composition formulated from an effective amount of a cellular extract of *Yersinia entomophaga* MH96 wherein said extract exhibits a biopesticide activity.

According to a further aspect of the present invention there is provided a composition formulated from an effective amount of a sonicated cell filtrate of *Yersinia entomophaga* MH96, wherein said extract exhibits a biopesticide activity.

Preferably, the composition may be formulated with at least one biopolymer compound. Preferably, at least one biopolymer compound is at least one type of gum compound.

Preferably, the composition may be formulated as a gel composition.

Preferably, the composition may be formulated with at least one biopolymer compound and at least one desiccating agent.

Preferably, the composition may be formulated with at least one type of gum compound and the at least one desiccating agent is at least one inert clay compound.

Preferably, the composition may be formulated as a dough or granular material.

Preferably, the composition may be formed into a prill or granule shape.

Preferably, the composition may be mixed with an aqueous liquid and sprayed onto a substrate. Other embodiments, the composition may be coated onto a substrate. Preferably, the substrate may be a seed.

According to a further aspect of the present invention there is provided a method of treating or protecting a plant and/or plant derived materials from pest infestation wherein the method comprises applying to the plant or its environment an effective amount of *Yersinia entomophaga* MH96.

According to a further aspect of the present invention there is provided a method substantially as described above wherein the effective amount of *Yersinia entomophaga* MH96 is obtained from a culture of *Yersinia entomophaga* MH96.

According to a further aspect of the present invention there is provided a method substantially as described above wherein the effective amount of *Yersinia entomophaga* MH96 is obtained from a supernatant from a whole broth culture of *Yersinia entomophaga* MH96.

According to a further aspect of the present invention there is provided a method of treating or protecting a plant or plant derived materials from pest infestation wherein the method comprises applying to the plant or its environment an effective amount of a cellular extract of *Yersinia entomophaga* MH96.

According to a further aspect of the present invention there is provided a method of treating or protecting a plant and/or plant derived materials from pest infestation wherein the method comprises applying to the plant or its environment an effective amount of a sonicated cell filtrate of *Yersinia entomophaga* MH96.

According to a further aspect of the present invention there is provided a method of treating or protecting a plant and/or plant derived from pest infestation wherein the method comprises applying to the plant or its environment a composition comprising an effective amount of *Yersinia entomophaga* MH96.

According to a further aspect of the present invention there is provided a method substantially as described above wherein the effective amount of *Yersinia entomophaga* MH96 is obtained from a culture of *Yersinia entomophaga* MH96.

According to a further aspect of the present invention there is provided a method substantially as described above wherein the effective amount of *Yersinia entomophaga* MH96 is obtained from a supernatant from a whole broth culture *Yersinia entomophaga* MH96.

According to a further aspect of the present invention there is provided a method of treating or protecting a plant and/or plant derived materials from pest infestation wherein the method comprises applying to the plant or its environment a composition comprising an effective amount of a cellular extract of *Yersinia entomophaga* MH96.

According to a further aspect of the present invention there is provided a method of treating or protecting a plant and/or plant derived materials from pest infestation wherein the method comprises applying to the plant or its environment a composition comprising an effective amount of a sonicated cell filtrate of *Yersinia entomophaga* MH96.

According to a further aspect of the present invention there is provided a method of controlling and/or preventing a pest infestation characterised by the step of applying a composition comprising an effective amount of *Yersinia entomophaga* MH96 to a surface.

According to a further aspect of the present invention there is provided a method as claimed in claim 48, wherein the effective amount of *Yersinia entomophaga* MH96 is obtained from a culture of *Yersinia entomophaga* MH96.

According to a further aspect of the present invention there is provided a method as claimed in claim 48, wherein the effective amount of *Yersinia entomophaga* MH96 is obtained from a supernatant from a whole broth culture of *Yersinia entomophaga* MH96.

According to a further aspect of the present invention there is provided a method of controlling and/or preventing a pest infestation characterised by the step of applying a composition comprising an effective amount of a cellular extract of *Yersinia entomophaga* MH96 to a surface.

According to a further aspect of the present invention there is provided a method of controlling and/or preventing a pest infestation characterised by the step of applying a composition comprising an effective amount of a sonicated cell filtrate of *Yersinia entomophaga* MH96 to a surface.

According to a further aspect of the present invention there is provided a method of controlling and/or preventing a pest infestation characterised by the step of applying a composition as substantially described above, to a surface.

According to a further aspect of the present invention there is provided the use of an isolated *Yersinia entomophaga* MH96 bacterium deposited at DSMZ on 4 May 2006 and designated accession no. DSM 18238, or culture thereof, for use in the biopesticide activity against the insect species listed in Table 13 and/or the larvae thereof.

It should be appreciated by those skilled in the art that discovery by the inventors that *Yersinia entomophaga* MH96 has a biopesticide activity is of broad application.

Preferably, the biopesticide activity may be for the application against insect species listed in Table 13 and/or the larvae thereof.

As used herein the term "isolated" means removed from the natural environment in which the bacteria naturally occurs and is separated from some or all of the co-existing materials in the natural system from which the bacteria has been obtained.

As used herein the term "biopesticide" refers to a biologically derived substance having the ability to kill, or retard the growth of, insects and/or the larvae thereof. In particular, a biopesticide of the present invention should be capable of retarding growth, or killing, one or more of the insect species listed in Table 13 and/or the larvae thereof. Most preferably, a biopesticide of the present invention should be capable of retarding the growth, or killing, at least one, but preferably all or most of the species listed in Table 13 and/or the larvae thereof.

As used herein the term "culture" refers to a population of bacteria together with the media in or on which the population was propagated (i.e. grown).

As used herein the term "whole broth culture" refers to a liquid media and the population of bacteria therein.

In preferred embodiments the broth may be Luria-Bertani broth. However, it will be appreciated by a person skilled in the art that other suitable broths may be used.

As used herein the term "cellular extract" refers to a substance or mixture of substances obtained from a bacterial cell.

As used herein the term "sonicate" or grammatical variants thereof refers to subjecting a cell to ultrasonic vibrations in order to fragment the cell wall to release the contents of the cell.

It should be appreciated that the 'cellular extract' may be obtained in a variety of different ways, and may come in a variety of different forms without departing from the scope of the present invention.

In some embodiments the cellular extract may be a crude extract of the contents of the cell. In general the crude extract may be obtained via centrifugation of a whole broth culture re-suspended in a suitable buffer.

Such an extract may have been derived from Sonication; French press; Mantin gaulin press, bead basher, bead mill mincer osmotic lysis and enzyme related lysis as outlined in Scopes (1993); Doonan (1996) and Sambrook et al. (1989).

In other embodiments the cellular extract may be a freeze dried or a spray dried extract. In general, the freeze or spray dried extract may be obtained via any cellular extract which has also been subjected to a freeze- or spray drying process or alternate processes as outlined in Maa and Prestrelski (2000).

In preferred embodiments the cellular extract may be derived from the aforementioned methods via sonication; French press; Mantin gaulin press, bead basher, bead mill mincer osmotic lysis or enzyme related lysis.

In general the inventors have found that a supernatant having a biopesticide activity will be obtained when the organism is grown in Luria-Bertani broth at 25° C.

The term 'plant' refers to the plant in it's entirety or a part thereof including selected portions of the plant during the plant life cycle such as the plant seeds, shoots, leaves, bark, pods, roots, flowers, stems and the like, including crop food and plant derived materials or parts thereof.

The term 'plant derived materials' refers to products that may be produced from a plant or part thereof. It will be appreciated that a person skilled in the art will know of various examples of plant derived products, such as hay, silage or other types of feed or products.

Compositions of the present invention may be formulated in a variety of different ways without departing from the scope of the present invention. In general the formulation chosen will be dependent on the end application. For example, possible formulations include, but should not be limited to:

Vectors such as the Trojan vector;
Matrixes;
Soluble powders;
Granules;
Micro encapsulation in a suitable medicine;
Aqueous suspensions;
Non-aqueous suspensions;
Emulsions;
Pastes;
Emulsifiable concentrations; or
Baits.

The present invention may preferably include formulations suitable for:

direct application to insect affected areas e.g. drench, spray form;
suspended in a bait matrix;
slow release prills for subterranean applications; or
hydrophobic matrixes facilitating buoyancy for aquatic surface filter feeders.

It will be appreciated that other suitable formulations and/or methods of preparing the formulations and/or compositions will be known to those skilled in the art. Examples of other such methods to stabiles or prepare a composition include the methods described in patent applications WO 02/15702 or WO 02/15703.

The term bait as used herein refers to any foodstuff or other attractant to an insect or larvae thereof whith includes an effective amount of:

a) *Yersinia entomophaga* MH96; or
b) a mutant or variant strain of *Yersinia entomophaga* MH96; or
c) a derivative of a) or b).

The term 'effective amount' as used herein refers to a suitable quantity for a biopesticide activity to be exhibited.

The *Yersinia entomophaga* MH96 of the present invention produces a biopesticide which can be applied directly to surfaces where insects may contact such as artificial/cultural surfaces (e.g. milled wood, concrete, and urban dwellings); as well as in agricultural systems such as plant surfaces seed coats or matter of plant origin.

The present invention has application in both terrestrial and aquatic environments and may be applied in or on both soil and phylloplane or rhizospere systems.

Thus, preferred embodiments of the present invention may have a number of advantages over the prior art which can include:

providing a new biopesticide which has a broad efficacy across a range of insects;
providing a new method for controlling insects; and
providing a new biopesticide which has a range of different forms.

BRIEF DESCRIPTION OF DRAWINGS

Further aspects of the present invention will become apparent from the following description which is given by way of example only and with reference to the accompanying drawings in which:

Figure 5:
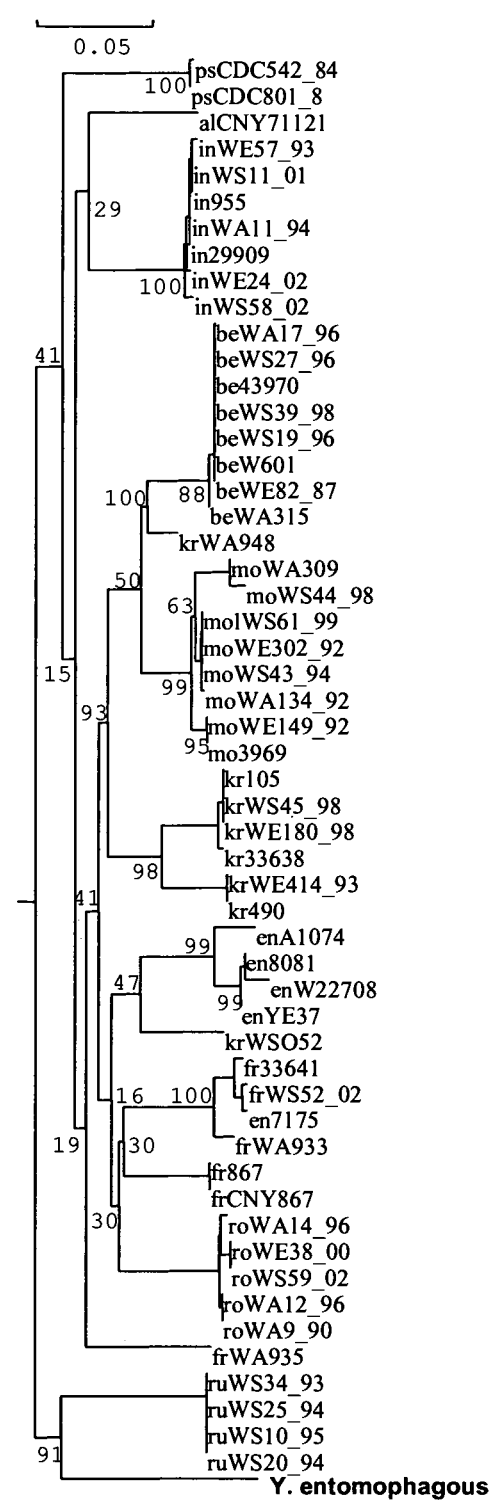

FIG. 5 shows a phylogenetic comparison based on data from amplification of 394 bp from recA, analysed using the programme DNAman, tree created using the Neighbor-Joining method (Saitou and Nei, 1987, Mol. Biol. Ecol. 4:406-425) (data from Kotetishvili et. al 2005; except for *Yersinia entomophaga* MH96);

BEST MODES FOR CARRYING OUT THE INVENTION

Discovery

Figure 1:
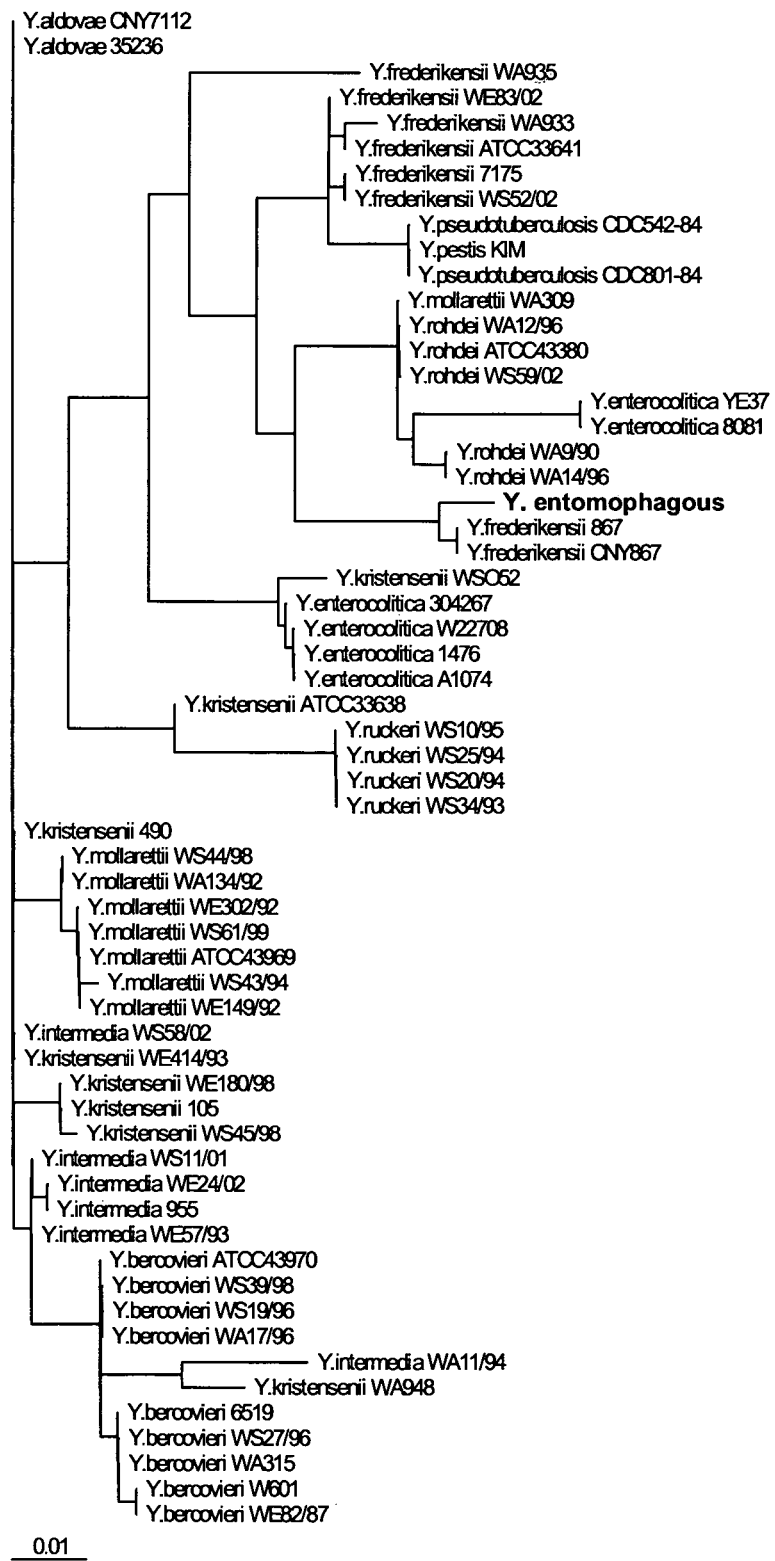
FIG. 1 shows a phylogenetic comparison of 16s ribosomal DNA of species within the genus *Yersinia*, using the program DNAML (Phylip suite) with default values, and with randomised input order (data from Kotetishvili et. al 2005; except for *Yersinia entomophaga* MH96)

During routine prefeeding assays of grass grub larvae that had been collected from various field locations throughout the South Island of New Zealand, larvae that appeared diseased were put aside and assessed for the presence of a causative bacterial agent.

Larvae were surface sterilized by submerging in 70% methanol. The larvae were then shaken in sterile DH$_2$O, removed and blotted dry. A 10 µl pipette tip was inserted through the back of the larvae breeching the haemocoelic cavity, an aliquot withdrawn and serial diluted in Luria Bertini broth. The diluent was plated on non-selective Luria Bertina media and incubated at 30° C. Morphologically different isolates were purified, and accessed for virulence by standard bioassay.

EXAMPLE 1

Physiological and Metabolic Characterisation

Gram Negative Rod

Growth in LB media with subsequent plating, shows that two colony forms are apparent these are:

i) convex circular ii) dimpled circular

However, if the colonies are allowed to grow to over 3-4 days all colonies have exhibit a convex circular form indicative that the dimpled circular form is growth stage dependant The bacteria exhibits growth retardation if grown at 37° C.

The bacteria form large flocs of bacterial cells in the RSYE culture grown at 37° C. just prior to 6 hours at 250 rpm.

Dilution plated samples taken at 48 and 72 hours required longer incubation at 30° C. before colonies were visible and able to be counted.

The colonies are positive on DNAase plates within 24 hours (O'Callaghan and Jackson 1993).

TABLE 1

ASSILMIATION TESTS AND RESULTS

| Test | Result |
|---|---|
| Gram stain | negative |
| Oxidase | negative |
| Glucose acid | positive |
| API 20E | 1-307-160 No match |
| DNAase | weak positive |

The strains were tested using a commercial bacterial identification system API, bio-Merieux. Results are shown in Table 2 below.

Carbon source utilisation tests were done by using API strips (API system, La Balme les Grottes, France)

TABLE 2

Testing results from AP1 bacterial identification system

| API | *Y. entomophaga* |
|---|---|
| ONPG (beta-galactosidase) | + |
| ADH (arginine dehydrolase) | − (weak) |
| LDC (lysine decarboxylase) | − |
| ODC (orthinine decarboxylase) | + |
| CIT (citrate utilisation) | + |
| $H_2S$ ($H_2S$ production) | − |
| URE (urease) | − |
| TDA (tryptophane desaminase) | − |
| IND (indole production) | − |
| VP (acetoin production) | + |
| GEL (gelatinase) | + |
| GLU (glucose fermentation) | + |
| MAN (mannitol fermentation) | + |
| INO (inositol fermentation) | − |
| SOR (sorbitol fermentation) | − |
| RHA (rhamnose fermentation) | − |
| SAC (sucrose fermentation) | + |
| MEL (melibiose fermentation) | + |
| AMY (amygdalin fermentation) | − |
| ARA (arabinose fermentation) | − |
| OX (oxidase) | − |
| DNAse | + |
| glycerol | + |
| erythritol | − |
| D-arabinose | − |
| L-arabinose | − |
| ribose | + |
| D-xylose | − |
| L-xylose | − |
| adonitol | − |
| β methyl-xyloside | − |
| galactose | + |
| D-glucose | + |
| D-fructose | + |
| D-mannose | + |
| L-sorbose | − |
| Rhamnose | − |
| Dulcitol | − |
| inositol | − |
| mannitol | + |
| Sorbitol | − |
| α methyl-D-mannoside | − |
| α methyl-D-glucoside | − |
| N acetyl glucosamine | + |
| amygdaline | − |
| arbutine | − |
| esculine | − |
| salicine | − |
| cellobiose | ? |
| maltose | + |
| lactose | ? |
| melibiose | + |
| saccharose | + |
| trehalose | + |
| inuline | − |
| melezitose | − |
| D-raffinose | + |
| amidon | − |
| glycogene | − |
| xylitol | − |
| β gentiobiose | − |
| D-turanose | − |
| D-lyxose | − |
| D-tagatose | − |
| D-fucose | − |
| D-arabitol | − |
| L-arabitol | − |
| gluconate | ? |
| 2 ceto-gluconate | − |
| 5 ceto-gluconate | ? | score api 50 = +24 hours (ATCC cultures >48 hrs).

? denotes inconclusive result.

TABLE 3

AGAR phenotypes of *Yersinia entomophaga* MH96 grown on various commercially supplied agar (Fort Richards) bacteria grown for 24 hours at 30° C.

| Plate media | Phenology |
|---|---|
| Orientation agar | purple |
| XLD agar | orange slight yellow halo |
| Col sheep blood | no lysis |
| Col horse blood | no lysis |
| Violet red bile agar | growth |
| Brilliant green agar modified | yellow |
| PFA agar | no growth |
| Dermatophte test medium | turquoise |
| Chocolate sens | matt rhizoid morphology |
| Cetrimide agar | no growth but very slight after 48 hours |
| Bismuth sulphite agar | dark green |

TABLE 3-continued

| AGAR phenotypes of *Yersinia entomophaga* MH96 grown on various commercially supplied agar (Fort Richards) bacteria grown for 24 hours at 30° C. | |
|---|---|
| Plate media | Phenology |
| Macconkey agar w/d cv | orangly matt rhizoid morphology |
| Haemin agar | no lysis |
| Brilliant green agar | light green tinge rhizoid growth |
| Thayer martin agar | no growth |

EXAMPLE 2

Genetic Identification

DNA-DNA Hybridization

DNA-DNA hybridization was determined at the Deutsche Sammlung von Mikroorganismen und. Zellkulturen, Braunschweig, Germany and carried out as described by De Ley et al. (1970) under consideration of the modifications described by Huss et al. (1983) using a model Cary 100 Bio UVNIS-spectrophotometer equipped with a Peltier-thermostatted 6×6 multicell changer and a temperature controller with in-situ temperature probe (Varian). DNA-DNA relatedness was tested at 70° C. in 2×SSC plus 10% (v/v) DMSO

TABLE 4

| % DNA-DNA similarity (in 2 X SSC at 70° C.) | |
|---|---|
| | "*Y. entomophaga* MH96" DSM 18238 (1006-840) |
| *Yersinia pseudotuberculosis* DSM $8992^T$ (ID 06-841) | 23.0 (19.7) |
| *Yersinia ruckeri* DSM $18506^T$ (ID 06-842) | 45.6 (52.1) |
| *Yersinia intermedia* DSM $18517^T$ (ID 06-843) | 0.82 (2.15) |

Results derived indicate that *Y. entomophaga* MH96 DSM 18238 (ID 06-840) does neither belong to the species *Y. pseudotuberculosis* DSM $8992^T$ (ID 06-841) nor to the species *Y. ruckeri* DSM $18506^T$ (ID 06-842) and nor to the species *Y. intermedia* DSM $18517^T$ (ID 06-843) when the recommendations of a threshold value of 70% DNA-DNA similarity for the definition of bacterial species by the ad hoc committee (Wayne et al., 1987) are considered.

DNA G+C Content

The DNA G+C content of *Yersinia entomophaga* MH96 DSM 18238 (ID 06-840): was determined at the Deutsche Sammlung von Mikroorganismen und Zellkulturen, Braunschweig, Germany according to the method of Mesbah et al. (1989) and as three independent measurements. Cells were disrupted using a French pressure cell and the DNA was purified according to the procedure of Cashion et al. (1977) and degraded as described by Mesbah et al. (1989) and assessed by HPLC system (Shimadzu Corp. Japan). Using this method the The DNA G+C content of *Y. entomophaga" MH*96 DSM 18238 (ID 06-840): was at 49.3 mol % G+C These estimates are within the accepted limits for the genus *Yersinia* of 46-50 mol % (Bercovier & Mollaret, 1984.).

Plasmid Visualisation

Plasmid visualisation by method of Kado and Lui (1981) showed that no extra-chromosomal elements such as plasmids were present.

Purification of Genomic Dna

Genomic DNA for rRNA sequencing was isolated by a modified method of Cathala G et al, (1983). A 1.5 ml O/N culture was pelletted, and resuspended in 500 μl of lysis solution (5M guanidine isothiocyanate, 10 mM EDTA, 50 mM Tris-HCl (pH 7.5), 8% mercaptoethanol). An equal volume of phenol:chloroform was added, the tube inverted several times and centrifuged at 13000 g for 15 minutes. The upper layer removed to a new eppendorf and ethanol precipitated. To remove residual Guandium and other inhibitory compounds, the resultant pellet was air dried and resuspended in 500 μl of $DH_2O$, placed in a 37° C. water bath, and intermittently agitated for 1-2 hours. The solution was then re-ethanol precipitated and resuspended in 50 μl $DH_2O$ rRNA PCR Closely related strains identified by API were obtained from the American Type Culture Collection, Md., and included the *Enterobacter sakazakii* strains ATCC29004 and ATCC51329.

The 16S gene was amplified with primers as shown in Table 5.

TABLE 5

| Primers used to amplify 16s rRNA | |
|---|---|
| U16a | AGA GTT TGA TCC TGG CTC |
| U16b | TAC GGY TAC CTT GTT ACG ACT T |
| UB16 A2 | GCC GCG GTA AT ACG GAG G |
| U16B2 | AGG ATA AGG GTT TGC GCT CCG |

PCR

94° C. 15 s 60° C. (30 s) 62° C. (2')×5 cycles

94° C. 15 s 57° C. (30 s) 62° C. (2')×40 cycles

PCR template was sequenced using automated sequencing and an Applied Biosystem 373A or 377 autosequencer. Sequence data was assembled using SEQMAN. The database at the National Centre for Biotechnology Information was searched using BLASTN and the WWW. Nucleotide sequence accession numbers. The sequences determined in this study have been assigned the GenBank accession numbers DQ400713-DQ400845.

rDNA Sequence Comparison

Table 6 below shows 16s comparison based on 1428 bp and compared with GenBank sequences:

TABLE 6

| 16s comparison based on 1428 bp and compared with GenBank sequences. | | | |
|---|---|---|---|
| Genbank accession number | Genus, species and strain | Reference/author | Accession date |
| AF366385 | *Yersinia ruckeri* | Kim, W., Song, M.-O., Song, W., Chung, S.-I., Choi, C.-S. and Park, Y.-H. | 8 MAY 2001 |

TABLE 6-continued 16s comparison based on 1428 bp and compared with GenBank sequences.

| Genbank accession number | Genus, species and strain | Reference/author | Accession date |
|---|---|---|---|
| AB004746 | Enterobacter sakazakii (strain: JCM1233) | Harada, H. | 25 JUL. 1997 |
| RAU90757 | Rahnella aquatilis | Brenner, D. J., Muller, H. E., Steigerwalt, A. G., Whitney, A. M., O'Hara, C. M. and Kampfer, P. (1998) Two new Rahnella genomospecies that cannot be phenotypically differentiated from Rahnella aquatilis. Int. J. Syst. Bacteriol. 48 Pt 1, 141-149 | 15 APR. 1998 |
| YEN16SA | Y. enterocolitica (strain O: 3 108 c) | Harmsen, D. | 27 JUN. 1996 |
| AF366384 | Yersinia rohdei 16S | Kim, W., Song, M.-O., Song, W., Chung, S.-I., Choi, C.-S. and Park, Y.-H. | 8 MAY 2001 |
| S000001663 | Yersinia pseudotuberculosis; Serotype III 1B1 B28 (W.W.) | Harmsen, D. W., Schmelz, J. F. and Heesemann, J. | 30 JUL. 1996 |
| S000001661 | Yersinia enterocolitica; ER-26036-92; serotype O: 3 | Ibrahim, A., Goebel, B. M., Liesack, W., Griffiths, M. and Stackebrandt, E. (1993) The phylogeny of the genus Yersinia based on 16S rDNA sequences. FEMS Microbiol. Lett. 114 (2), 173-177 | 12 JUN. 1995 |
| S000004821 | Yersinia pseudotuberculosis | Kim, W., Song, M.-O., Song, W., Chung, S.-I., Choi, C.-S. and Park, Y.-H. | 17 MAY 2001 |
| S000004821 | Yersinia pseudotuberculosis 83 | Kim, W., Song, M.-O., Song, W., Chung, S.-I., Choi, C.-S. and Park, Y.-H. | 17 MAY 2001 |
| S000003234 | Yersinia rohdei (T); ATCC 43380 | Kim, W., Song, M.-O., Song, W., Chung, S.-L, Choi, C.-S. and Park, Y.-H. | 8 MAY 2001 |
| YS17B16S | Yersinia sp. (isolate YEM17B | Ibrahim, A., Liesack, W., Steigerwalt, A. G., Brenner, D. J., Stackebrandt, E. and Robins-Browne, R. M. (1997) A cluster of atypical Yersinia strains with a distinctive 16S rRNA signature FEMS Microbiol. Lett. 146 (1), 73-78 | 17 FEB. 1997 |
| YPD16SRN | Yersinia pestis (D-28) | Ibrahim, A., Goebel, B. M., Liesack, W., Griffiths, M. and Stackebrandt, E. (1993) The phylogeny of the genus Yersinia based on 16S rDNA sequences. FEMS Microbiol. Lett. 114 (2), 173-177 | 27 MAY 2000 |
| AJ414156 | Yersinia pestis CO9 | | |
| YPE16SA | Y. pestis (strain EV pst+ c) | Harmsen, D. | |
| YEPRGD | Yersinia pestis | Wilson, K. H. and Hills, H. G. | 19 JAN. 1995 |
| AF365949 | Yersinia pseudotuberculosis strain 6088 | Kim, W., Song, M.-O., Song, W., Chung, S.-L, Choi, C.-S. and Park, Y.-H. | 17 MAY 2001 |
| YR16SRN | Yersinia rohdei (ER-2935) | Ibrahim, A., Goebel, B. M., Liesack, W., Griffiths, M. and Stackebrandt, E. (1993) The phylogeny of the genus Yersinia based on 16S rDNA sequences. FEMS Microbiol. Lett. 114 (2), 173-177 | 27 MAY 2000 |
| YK16SRRN | Yersinia kristensenii (ER-2812) kristensenii 2 | Ibrahim, A., Goebel, B. M., Liesack, W., Griffiths, M. and Stackebrandt, E. (1993) The phylogeny of the genus Yersinia based on 16S rDNA sequences. FEMS Microbiol. Lett. 114 (2), 173-177 | 27 MAY 2000 |

TABLE 6-continued 16s comparison based on 1428 bp and compared with GenBank sequences.

| Genbank accession number | Genus, species and strain | Reference/author | Accession date |
|---|---|---|---|
| AF366381 | Yersinia kristensenii | Kim, W., Song, M.-O., Song, W., Chung, S.-I., Choi, C.-S. and Park, Y.-H. | 8 MAY 2001 |
| AF366382 | Yersinia mollaretii Yersinia mollaretii2 | Kim, W., Song, M.-O., Song, W., Chung, S.-I., Choi, C.-S. and Park, Y.-H. | 8 MAY 2001 |
| YM16SRRN | Yersinia mollaretii (ER-2975) | Ibrahim, A., Goebel, B. M., Liesack, W., Griffiths, M. and Stackebrandt, E. (1993) The phylogeny of the genus Yersinia based on 16S rDNA sequences. FEMS Microbiol. Lett. 114 (2), 173-177 | 27 MAY 2000 |
| AF366379 | Yersinia frederiksenii | Kim, W., Song, M.-O., Song, W., Chung, S.-I., Choi, C.-S. and Park, Y.-H. | 8 MAY 2001 |
| AF366380 | Yersinia intermedia | Kim, W., Song, M.-O., Song, W., Chung, S.-I., Choi, C.-S. and Park, Y.-H. | 8 MAY 2001 |
| AF366376 | Yersinia aldovae | Kim, W., Song, M.-O., Song, W., Chung, S.-I., Choi, C.-S. and Park, Y.-H. | 8 MAY 2001 |
| YB16SRRN | Yersinia bercovieri Yersinia bercovieri 1 | Ibrahim, A., Goebel, B. M., Liesack, W., Griffiths, M. and Stackebrandt, E. (1993) The phylogeny of the genus Yersinia based on 16S rDNA sequences. FEMS Microbiol. Lett. 114 (2), 173-177 | 27 MAY 2000 |
| AF366377 | Yersinia bercovieri | Kim, W., Song, M.-O., Song, W., Chung, S.-I., Choi, C.-S. and Park, Y.-H. | 8 MAY 2001 |

Figure 2:
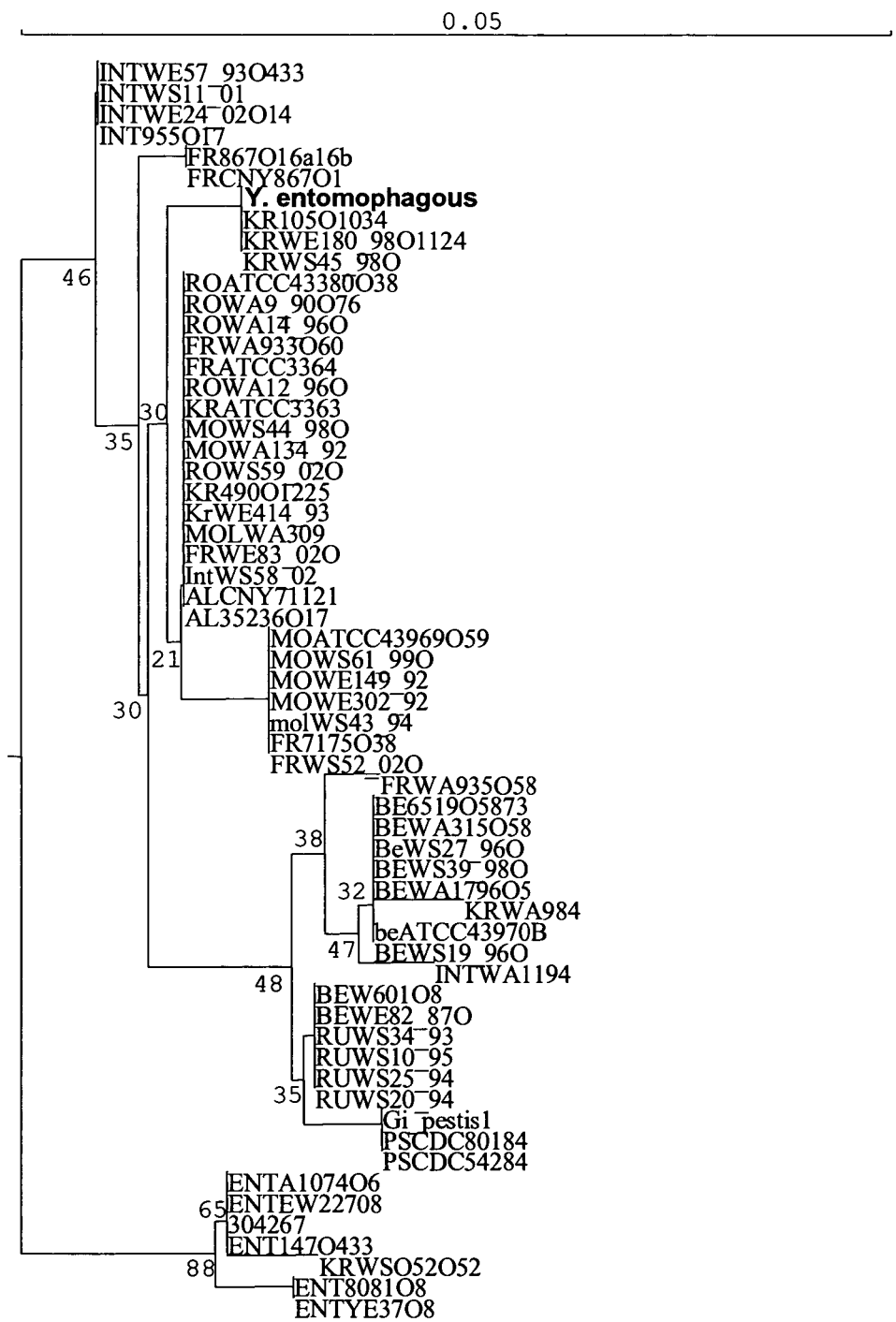
FIG. 2 shows a phylogenetic comparison of 16s ribosomal DNA based on amplification of 190 bp from 16s ribosomal DNA; based on 190 bp region analysed using the programme DNAman, tree created using the Neighbor-Joining method (Saitou and Nei, 1987, Mol. Biol. Ecol. 4:406-425)

As shown in FIGS. 1 and 2, using 16s rRNA sequences *Y. entomophaga* aligns with atypical strains of *Y. frederiksenii* (FIG. 1) or *Y. kristensenii* (FIG. 2—190 bp).

TABLE 7

Figure 3:
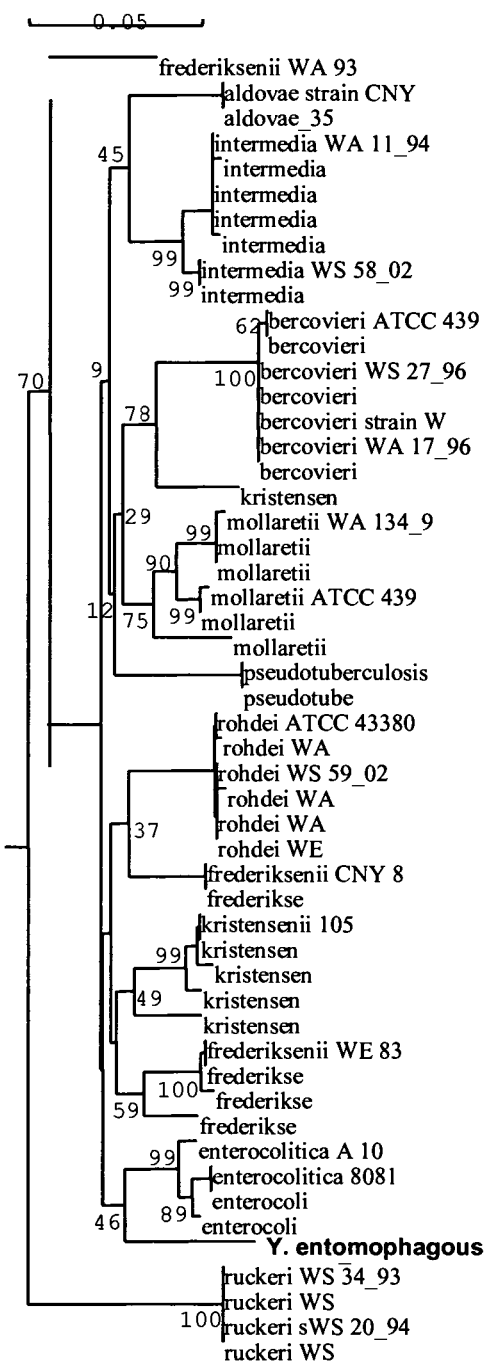
FIG. 3 shows a phylogenetic comparison based on data from 428 bp of Y-HSP60 amplification, analysed using the programme DNAman, tree created using the Neighbor-Joining method (Saitou and Nei, 1987, Mol. Biol. Ecol. 4:406-425) (data from Kotetishvili et. al 2005; except for *Yersinia entomophaga* MH96)
Figure 4:
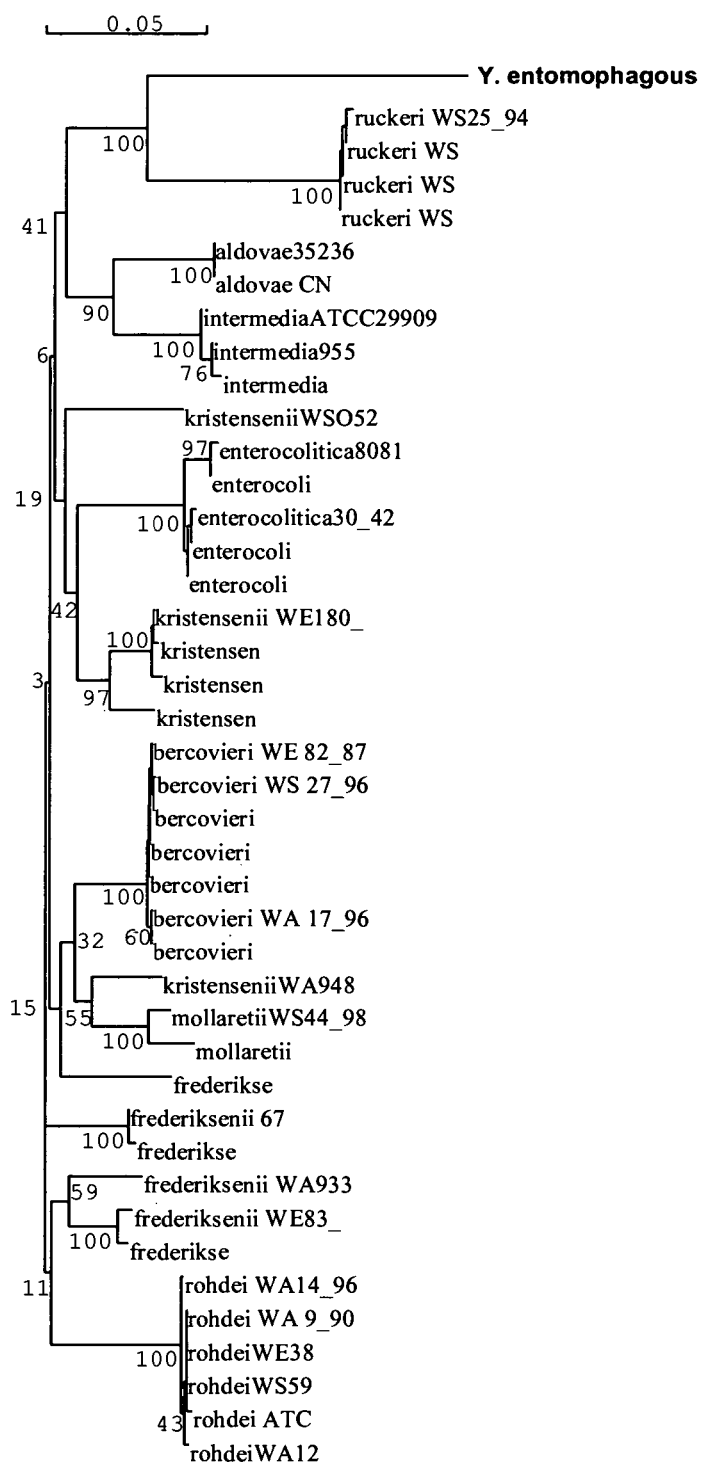
FIG. 4 shows a phylogenetic comparison based on data from glyA amplification, analysed using the programme DNAman, tree created using the Neighbor-Joining method (Saitou and Nei, 1987, Mol. Biol. Ecol, 4:406-425) (data from Kotetishvili et. al 2005; except for *Yersinia entomophaga* MH96)
Figure 6:
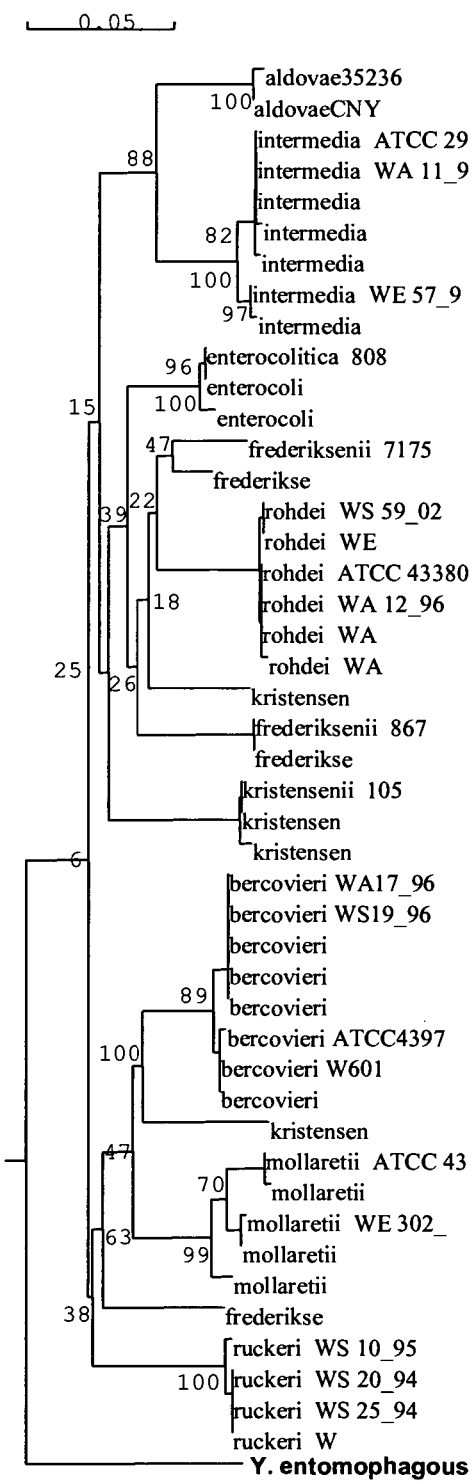
FIG. 6 shows a phylogenetic comparison based on data from gyrB amplification, analysed using the programme DNAman, tree created using the Neighbor-Joining method (Saitou and Nei, 1987, Mol. Biol. Ecol. 4:406-425) (data from Kotetishvili et, al 2005; except for *Yersinia entomophaga* MH96)
Figure 7:
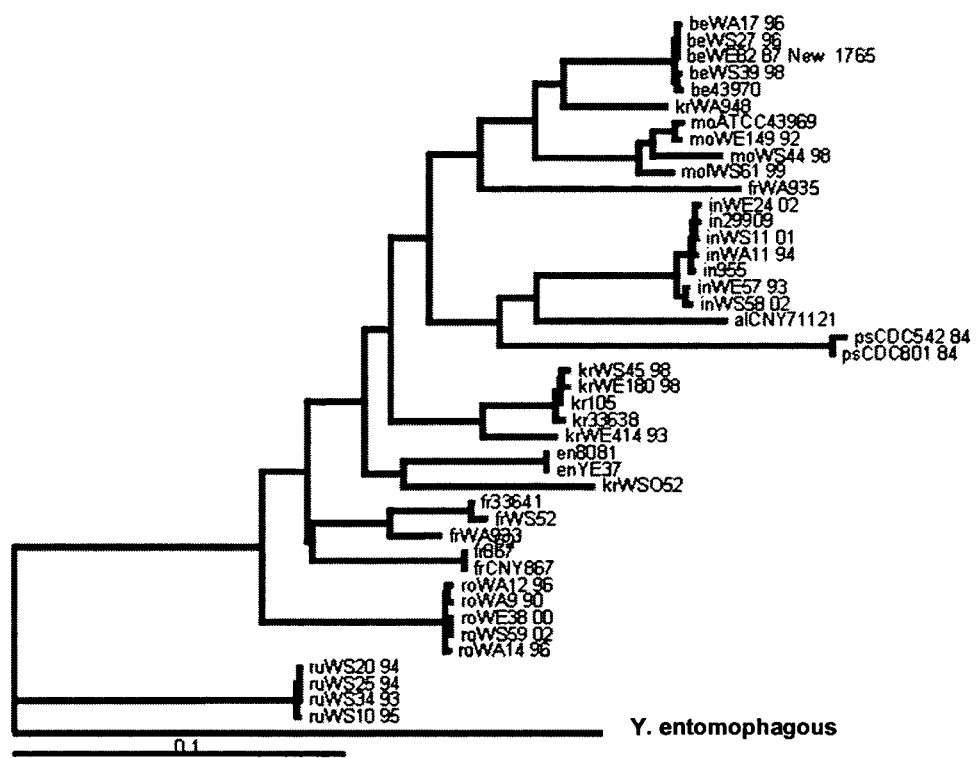
FIG. 7 shows a phylogenetic comparison based on data from amplification of 1765 bp assembled fragments, using the programme MrBayes v3.1.2 and trees viewed using TreeView (data from Kotetishvili et. al 2005; except for *Yersinia entomophaga* MH96)
Figure 8:
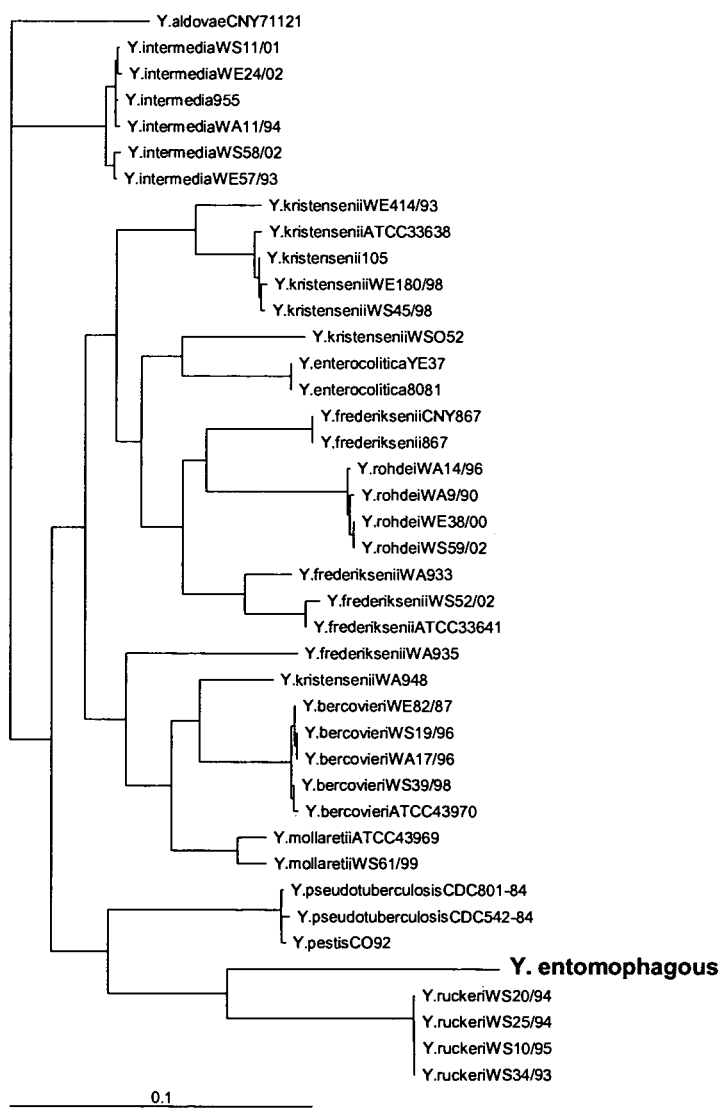
FIG. 8 shows a phylogenetic comparison based on data from amplification of GlnA, GyrB, RecA, Y-hsp60 (1,525 base) assembled fragments, analysed using a maximum likelihood tree using DNAML from the Phylip package (data from Kotetishvili et. al 2005; except for *Yersinia entomophaga* MH96)

Multi locus sequence tagging (MLST) Primers used for MLST of the Yersinia species (Derived from Kotetishvili et al. 200),

| Gene | Primers (5'→3') | Accession number and Results |
|---|---|---|
| 16S rDNA | AGTTTGATCATGGCTCAG TTACCGCGGCTGCTGGCA | DQ400782 FIG. 1 and 2 |
| GlnA | CGATTGGTGGCTGGAAAGGC TTGGTCATRGTRTTGAAGCG | DQ400780 FIG. 4 |
| GyrB | CGGCGGTTTGCAYGGYGTRGG CAGSGTRCGRGTCATYGCCG | DQ400781 FIG. 6 |
| recA | GGGCCAAATTGAAAARCARTTCGG CGCCRATYTTCATRCGRATYTGGT | DQ400835 FIG. 5 |
| Y-HSP60 | GACGTNGTAGAAGGTATGYAG CGCCGCCAGCCAGTTTAGC | DQ400829 FIG. 3 |

MLST analysis, based on primer sequences as above in Table 7, in conjunction and analysis of random genomic sequence analysis (Results shown in FIGS. 3-8 of phylogenetic comparison of sequences from the above genes), indicates that *Yersinia entomophaga* MH96 is a new species residing within the genera *Yersinia*. A presumptive name foe the new species would be *Yersinia entomophaga* MH96 (as it eats insects)

Random Genomic Sequencing of *Yersinia entomophaga* MH96

To further help define what species *Yersinia entomophaga* MH96 is, genomic DNA of *Yersinia entomophaga* MH96 was made and digested using the restriction enzymes HindIII; EcoRI and PstI in independent reactions. The digested DNA was then ligated to the vector DNA (pUC19) digested with the aforementioned enzymes. Using this method approximately 132 independent random HindIII; PstI; or EcoRI; clones were constructed. Using the pUC19 M13F and M13R based primers DNA from the clones was sequenced. The DNA sequence data has been deposited under the GenBank accession number (DQ400713-DQ400845). This data have enabled the generation of random snap shots of the *Yersinia entomophaga* MH96 genome and shown that many genes have greater than 90% DNA similarity to the DNA of *Yersinia pestis*. While other DNA remains at this point in time novel scoring no apparent similarity to DNA I the current database The DNA nucleotide sequence of 132 random *Y entomophaga* sequences have been submitted to GenBank and assigned the numbers DQ400713-DQ400845

EXAMPLE 3

Culture Conditions

*Yersinia entomophaga* MH96 can be grown in LB broth or on LB agar (Sambrook and Russell, 2001) or any alternate common laboratory media as yet no defined media for the isolation of *Yersinia entomophaga* MH96 has been defined, optimum growth for *Yersinia entomophaga* MH96 is 25° C.-30° C. Cultures were incubated at 200 rpm in a Raytek orbital mixer incubator.

Crude Toxin Isolation Using Cell Lysis Such as Sonication

From a 3 ml overnight culture pellet by centrifugation (8,000 g 3 minutes) resuspended in 1.0 ml of 1.5 ml phosphate buffer (10 mM phosphate buffer, pH 7.4; 2.7 mM KCl; 137 mM NaCl), two 0.7 ml samples were transferred to an eppendorf and subjected to three 30s rounds of sonication on wet ice using a Sanyo soniprep 150 sonicater (18Ω). The sonicated samples were centrifuged (16,000 g) and the supernatant filter sterilised through a 0.2 µm filter to a sterile eppendorf. The filtrate's were placed on wet ice and used immediately for bioassay analysis. The efficacy of the lysate was assessed by the oral injection of 5 µl of filtrate sample through the larval mouth parts or the application of 5 µl of filtrate sample to the surface of a 3 mm³ carrot from which the grass grub larvae would feed. Under these conditions toxins can be visualised on a standard Laemmli SDS-polyacrylamide gel electrophoresis (SDS-PAGE). The toxins have activity only if the bacterium is subjected to sonication. Bioassays of *Yersinia entomophaga* MH96 culture supernatant show no effect (refer Table 8-12).

Crude Toxin Isolation via *Y. entomophaga* MH96 Grown at 25° C.

Induction and Purification of *Y. entomophaga* MH96 Toxin

From an overnight culture grown at 25° C. Bacterial debris was removed by centrifugation (30 min; 12000 g; 4° C.) and the supernatant filter sterilised through a 0.2 µm filter to a sterile eppendorf.

Standard Bioassay

Healthy feeding larvae, collected from the field, were individually fed squares of carrot which had been rolled in colonies of putative pathogenic bacteria that had grown overnight on solid media. Twelve second or third instar larvae were used for each treatment. Inoculated larvae were maintained at 15° C., in ice-cube trays. Larvae were left feeding on treated carrot for 3-4 days, then transferred to fresh trays and re-fed with untreated carrot for up to 10-14 days and signs of disease noted.

Dose Response Assay

An overnight culture of bacteria was grown, and a dilution series set up in phosphate buffer. Five of each dilution were inoculated onto pre air dried carrot cubes measuring approximately 3 mm³. Grass grub were placed into each of the trays cubicles, and results monitored as previously described under standard bioassay.

Experimental Protocols

Testing of *Yersinia entomophaga* MH96 on the Diamond Backed Moth (DBM).

The bioassay of efficacy of *Yersinia entomophaga* MH96 live cells and the toxic proteins from *Yersinia entomophaga* MH96 was tested on the Diamond Backed Moth (DBM).

Five fractions of the bacterial culture tested:

1. Live cell broth; 1 ml freshly cultured broth used.
2. Concentrated live cells. 10 ml of broth centrifuged at 8000 rpm for 8 min, the resulting pellet harvested, and resupended in 1 ml of PB;
3. Resuspended live cells. 1 ml broth centrifuged at 8000 rpm for 8 min, the resulting pellet harvested and cells resuspended in equal volume of PB;
4. Heat killed broth. 1 ml broth subjected to boiling water for 10 min; broth plated out in LB plate to confirm if any live cells.
5. Sterile filtrate broth. 10 ml broth centrifuged at 8000 rpm for 8 min, the resulting pellet harvested, resuspended in 1 ml PB, then sonicated and centrifuged at 1300 rpm, 5 min; the supernatant harvested. Supernatant plated out in LB plate to confirm if any live cells.

All fractions mixed with 0.2% Tween 80 as emulsifier. LB broth and PB plus 0.2% Tween 80 used as controls.

Assessment: Leaf Disc Method.

1. The 2$^{nd}$ to 4$^{th}$ instars collected from plants and place in a container supplied with cabbage leaves. If not enough for an experiment, larvae stored in fridge for an extended 2 to 3 day period until further collections.
2. Larvae transferred to clean or sterile Petri dishes containing no cabbage leaves by a sterile fine art brush at least 4 h prior to being exposed to treatments to ensure sufficient uptake of bacteria and the fractions tested.
3. Leaf discs (1.0 cm in diameter) punctured from tender leaves of cabbage seedlings, and stored in a Petri dish containing a small piece of wet tissue
4. Using freshly flame sterilized soft tweezers transfer the leaf discs individually into the wells of plates, with the upper surface of the leaves upward.
5. 5 µl of test suspension pipetted onto the upper surface of the leaf disc and spread with a sterile glass rob or homogenizer.
6. Larvae transferred individually onto a leaf disc with alcohol sterilized fine art brushes carefully. All larvae used for a treatment pooled in a plate covered by parafilm to prevent larval escaping from wells.
7. Recode the developmental stage of each larva.
8. Plates sealed in plastic bags and held at 15 C under 14:10 (L:D) h photoperiod.
9. Leaf discs renewed daily using the method above. Mortality monitored within 5 d post-inoculation.

8-12 larvae tested for each treatment, Experiments carried out three replications.

Summary

Pathogenicity of Bacteria *Yersinia entomophaga* MH96 to Diamond Back Moth, *Plutella xylostella* (L.)

Laboratory Bioassay of *Yersinia entomophaga* MH96 Toxicity to DBM Larvae

Determination of active fractions

TABLE 8

Effect of the culture broth fractions of *Yersinia entomophaga* MH96 on the mortality of diamond back moth larvae.

| Fraction | Rep* | No. larvae tested | No. dead larvae | Mortality (%) | Mean (%) |
|---|---|---|---|---|---|
| Live cell broth | 1 | 10 | 10 | 100.0 | |
| | 2 | 12 | 12 | 100.0 | |
| | 3 | 12 | 12 | 100.0 | |
| | 4 | 12 | 12 | 100.0 | 100.0 |
| Resuspended live cells | 1 | 10 | 10 | 100.0 | |
| | 2 | 12 | 11 | 91.7 | |
| | 3 | 12 | 12 | 100.0 | |
| | 4 | 12 | 11 | 91.7 | 95.8 |
| Heat killed broth | 1 | 10 | 2 | 20.0 | |
| | 2 | 12 | 0 | 0.0 | |
| | 3 | 12 | 0 | 0.0 | |
| | 4 | 12 | 1 | 8.3 | 7.1 |
| Sonicated cell filtrate | 1 | 10 | 10 | 100.0 | |
| | 2 | 12 | 12 | 100.0 | |
| | 3 | 12 | 11 | 91.7 | |
| | 4 | 12 | 11 | 91.7 | 95.8 |
| Broth supernatant | 1 | 10 | 0 | 0.0 | |
| | 2 | 12 | 0 | 0.0 | |
| | 3 | 12 | 0 | 0.0 | |
| | 4 | 12 | 0 | 0.0 | 0.0 |
| Control 1 (PBS) | 1 | 10 | 2 | 20.0 | |
| | 2 | 12 | 0 | 0.0 | |
| | 3 | 12 | 0 | 0.0 | |
| | 4 | 12 | 0 | 0.0 | 5.0 |

TABLE 8-continued

Effect of the culture broth fractions of *Yersinia entomophaga* MH96 on the mortality of diamond back moth larvae.

| Fraction | Rep* | No. larvae tested | No. dead larvae | Mortality (%) | Mean (%) |
|---|---|---|---|---|---|
| Control 2 (LB broth) | 1 | 10 | 1 | 10.0 | |
| | 2 | 12 | 0 | 0.0 | |
| | 3 | 12 | 0 | 0.0 | |
| | 4 | 12 | 0 | 0.0 | 2.5 |

Screenings of $LD_{50}$ of active fractions
Live cell broth

TABLE 9

Effect of *Yersinia entomophaga* MH96 dose on the mortality of diamond back moth larvae.

| Dilution series tested | Rep | Dose (cells/cm²) | No. larvae tested | No. dead larvae | No. dead pupae | Mortality (%) | Mean (%) |
|---|---|---|---|---|---|---|---|
| $10^0$ | 1 | 28000000 | 12 | 12 | 0 | 100.0 | |
| | 2 | 21000000 | 12 | 11 | 0 | 91.7 | |
| | 3 | 31000000 | 12 | 11 | 0 | 91.7 | 94.4 |
| $10^{-1}$ | 1 | 2800000 | 12 | 8 | 2 | 83.3 | |
| | 2 | 2100000 | 12 | 10 | 0 | 83.3 | |
| | 3 | 3100000 | 12 | 12 | 0 | 100.0 | 88.9 |
| $10^{-2}$ | 1 | 280000 | 12 | 9 | 0 | 75.0 | |
| | 2 | 210000 | 12 | 7 | 3 | 83.3 | |
| | 3 | 310000 | 12 | 9 | 2 | 91.7 | 83.3 |
| $10^{-3}$ | 1 | 28000 | 12 | 7 | 0 | 58.3 | |
| | 2 | 21000 | 12 | 4 | 1 | 41.7 | |
| | 3 | 31000 | 12 | 6 | 3 | 75.0 | 58.3 |
| $10^{-4}$ | 1 | 2800 | 12 | 5 | 3 | 66.7 | |
| | 2 | 2100 | 12 | 5 | 2 | 58.3 | |
| | 3 | 3100 | 12 | 2 | 2 | 33.3 | 52.8 |
| $10^{-5}$ | 1 | 280 | 12 | 6 | 1 | 58.3 | |
| | 2 | 210 | 12 | 2 | 2 | 33.3 | |
| | 3 | 310 | 12 | 1 | 2 | 25.0 | 38.9 |
| Control | 1 | 0 | 12 | 0 | 0 | 0.0 | |
| | 2 | 0 | 12 | 0 | 0 | 0.0 | |
| | 3 | 0 | 12 | 0 | 0 | 0.0 | 0.0 |

Sonicated cell filtrate

TABLE 10

Effect of the sonicated cell filtrate concentration of *Yersinia entomophaga* MH96 on mortality of diamond back moth larvae.

| Concentration | Rep | No larvae tested | No dead larvae | No dead pupae | Mortality (%) | Mean (%) |
|---|---|---|---|---|---|---|
| 100% | 1 | 12 | 11 | 0 | 91.7 | |
| | 2 | 12 | 11 | 0 | 91.7 | |
| | 3 | 12 | 10 | 1 | 91.7 | 91.7 |
| 50% | 1 | 12 | 6 | 1 | 58.3 | |
| | 2 | 12 | 11 | 0 | 91.7 | |
| | 3 | 12 | 11 | 0 | 91.7 | 80.6 |
| 20% | 1 | 12 | 9 | 0 | 75.0 | |
| | 2 | 12 | 9 | 0 | 75.0 | |
| | 3 | 12 | 7 | 2 | 75.0 | 75.0 |
| 10% | 1 | 12 | 5 | 0 | 41.7 | |
| | 2 | 12 | 7 | 0 | 58.3 | |
| | 3 | 12 | 8 | 1 | 75.0 | 58.3 |
| 2% | 1 | 12 | 2 | 0 | 16.7 | |
| | 2 | 12 | 3 | 0 | 25.0 | |
| | 3 | 12 | 5 | 1 | 50.0 | 30.6 |
| 1% | 1 | 12 | 0 | 0 | 0.0 | |
| | 2 | 12 | 0 | 0 | 0.0 | |
| | 3 | 12 | 1 | 0 | 8.3 | 2.8 |
| Control | 1 | 12 | 0 | 0 | 0.0 | |
| | 2 | 12 | 0 | 0 | 0.0 | |
| | 3 | 12 | 0 | 0 | 0.0 | 0.0 |

Screenings of stability of active fractions
Live cell broth

TABLE 11

Effect of ambient temperature and length of storage period on toxicity of *Yersinia entomophaga* MH96 live cells to DBM larvae

| Treatment | Rep | No larvae tested | No dead larvae | Mortality (%) | Mean (%) |
|---|---|---|---|---|---|
| 0 d (Fresh culture) | 1 | 12 | 11 | 91.7 | |
| | 2 | 12 | 10 | 83.3 | |
| | 3 | 12 | 9 | 75.0 | 83.3 |
| 1 d, 20° C. | 1 | 12 | 12 | 100.0 | |
| | 2 | 12 | 10 | 83.3 | |
| | 3 | 12 | 9 | 75.0 | 86.1 |
| 7 d, 20° C. | 1 | 12 | 10 | 83.3 | |
| | 2 | 12 | 11 | 91.7 | |
| | 3 | 12 | 7 | 58.3 | 77.8 |
| 1 d, 4° C. | 1 | 12 | 8 | 66.7 | |
| | 2 | 12 | 7 | 58.3 | |
| | 3 | 12 | 8 | 66.7 | 63.9 |
| 7 d, 4° C. | 1 | 12 | 10 | 83.3 | |
| | 2 | 12 | 11 | 91.7 | |
| | 3 | 12 | 11 | 91.7 | 88.9 |
| Control | 1 | 12 | 0 | 0.0 | |
| | 2 | 12 | 1 | 8.3 | |
| | 3 | 12 | 1 | 8.3 | 5.6 |

Sonicated cell filtrate

TABLE 12

Effect of temperature and length of storage period on toxicity of *Yersinia entomophaga* MH96 sonicated cell filtrate to DBM larvae

| Treatment | Rep | No larvae tested | No dead larvae | Mortality (%) | Mean (%) |
|---|---|---|---|---|---|
| 0 d (Fresh culture) | 1 | 12 | 12 | 100.0 | |
| | 2 | 12 | 9 | 75.0 | |
| | 3 | 12 | 11 | 91.7 | 88.9 |
| 1 d, 20° C. | 1 | 12 | 11 | 91.7 | |
| | 2 | 12 | 9 | 75.0 | |
| | 3 | 12 | 11 | 91.7 | 86.1 |
| 7 d, 20° C. | 1 | 12 | 12 | 100.0 | |
| | 2 | 12 | 10 | 83.3 | |
| | 3 | 12 | 11 | 91.7 | 91.7 |
| 1 d, 4° C. | 1 | 12 | 8 | 66.7 | |
| | 2 | 12 | 9 | 75.0 | |
| | 3 | 12 | 7 | 58.3 | 66.7 |
| 7 d, 4° C. | 1 | 12 | 11 | 91.7 | |
| | 2 | 12 | 8 | 66.7 | |
| | 3 | 12 | 9 | 75.0 | 77.8 |
| Control | 1 | 12 | 1 | 8.3 | |
| | 2 | 12 | 0 | 0.0 | |
| | 3 | 12 | 1 | 8.3 | 5.6 |

Bait Formulation of *Yersinia entomophaga* Mh96 Against $7^{TH}$-$8^{TH}$ Instar *Wiseana* Sp Larvae Experiment 1

Method

*Wiseana* spp. *larvae* (most likely *W. copularis* based on size and flight times of moths in January) were collected from pasture on Taieri Plain. The moths were housed in 60 ml specimen containers three quarters filled with ground pine bark (<2 mm) to which were added white clover (*Trifolium repens* var. Huia) leaves as food. This food was changed every 3-4 days and the larvae moved to fresh containers after three weeks and again one day prior to the commencement of the bioassay.

For the bioassay, ten larvae were randomly allocated to be given *Yersinia entomophaga* MH96 kibbled wheat baits and ten allocated as controls. Those larvae in the *Yersinia entomophaga* MH96 treatment were given approximately ½ teaspoon of kibbled wheat (8-12 grains) while the control larvae continued to be given clover leaves. Larval survival and feeding was assessed after five days and again at ten days. Surviving larvae were fed again after five days according to treatment.

Results

After five days, six of the *Wiseana* spp. *larvae* given *Yersinia entomophaga* MH96 were dead while all the control larvae were alive and apparently healthy. After ten days all larvae given *Yersinia entomophaga* MH96 had died and all control larvae were alive. On both occasions the larvae given kibbled wheat had taken it into their burrows and signs of feeding were evident.

Conclusion

*Yersinia entomophaga* MH96 treated kibbled wheat was associated with the deaths of *Wiseana* spp. *larvae*.

Experiment 2

Introduction

The earlier laboratory bioassay in Experiment 1 above showed that the *Yersinia entomophaga* MH96 treatment caused mortality of large and small *Wiseana* spp larvae. However these bioassays were carried out using treated kibbled wheat where no alternative food source for the larvae was available, as the larvae were exposed to the baits and in small 60 ml specimen containers. Therefore, the current experiment was aimed to test the effectiveness of *Yersinia entomophaga* MH96 treatment under a more realistic situation where the larvae had an alternative food supply and could more easily avoid contact with the baits.

Method

Figure 9:
FIG. 9 shows clover seedlings cut to approximately 10 mm, and Kibbled wheat baits can be seen on the surface of the potting mix.

Ten containers with transparent acrylic sides and measuring 500(l)×300(w)×300(h) mm (FIG. 9) were filled to a depth of 150 mm with fine (<3 mm) pine bark. A 30-40 mm layer of Yates™ potting mix was applied over the bark surface. Twelve *Trifolium repens* seedlings were planted into each of the ten containers and allowed to establish. The seedlings were held in a white shade-cloth covered tunnel house at ambient air temperature which was measured by two "Tiny Tag" temperature data loggers. Five days after planting, ten final instar stage *Wiseana* spp. *larvae* collected and placed in each container.

At 14 days after planting, the seedlings were cut to approximately 10 mm high (FIG. 9). *Yersinia entomophaga* MH96 broadcast kibbled wheat baits where applied to the surface of five of the containers at a rate equivalent to 50 kg baits/ha (0.83 g/container). The remaining five containers were untreated (controls).

The clover plants were assessed for survival 12 days after the application of *Yersinia entomophaga* MH96 broadcast kibbled wheat baits. A second application of bait was made 13 days after the first application and plant survival assessed again 25 days after the initial application. The plants were harvested (cut to "ground" level) two days later and dried at 80° C. overnight to assess dry matter production over the duration of the experiment. The containers were also broken down at this time and the potting mix/bark searched for *Wiseana* spp. *larvae*. The data were analysed by one way analyses of variance with no blocking (Genstat version 8).

Results

Figure 10:
FIG. 10 shows clover plants at day 12, container A had four plants destroyed by *Wiseana* spp. *larvae* feeding, while all the plants survived in the container B on the right.
Figure 10:

Although *Wiseana* spp. *larvae* destroyed some plants (Table 13, and FIG. 10) overall there were few differences in plant survival between treatments or assessment times. Plant survival was higher on both occasions in the containers treated with the bait, but this difference was not significant (Table 13 ($P<0.13$, $P<0.08$, first and second assessments respectively)).

There was no difference in clover production between the baited treatment and the control treatments (Table 13 ($P<0.54$)). Although survival of larvae was significantly higher in the control containers compared to those treated with the bait. (Table 13 ($P<0.001$)) it is probable that the warm temperatures and high nutrient status of the potting mix allowed the clover plants in those containers with high numbers of larvae to outgrow and compensate for the affects of larvae feeding.

The *Wiseana* spp larvae survival in the control containers was approximately 46%, and is considered to be satisfactory for field collected larvae and average density in these containers equated to 31 larvae/m$^2$. This would be a moderate field density but the vegetation within the containers was sparse relative to pasture. The reduction in larvae numbers associated with the *Yersinia entomophaga* MH96 application was approximately 78%.

TABLE 13

Plant survival and production and *Wiseana* spp larvae survival (mean) over the duration of the bioassay.

| | No plants Day 12 | No plants Day 25 | Dry Matter (g) Day 27 | Live Larvae Day 27 |
|---|---|---|---|---|
| Bait Treatment | 11.6 | 11.6 | 11.2 | 1.0 |
| Control | 10.2 | 10.2 | 10.3 | 4.6 |
| SED | 0.8 | 0.7 | 1.3 | 0.5 |

Figure 11:
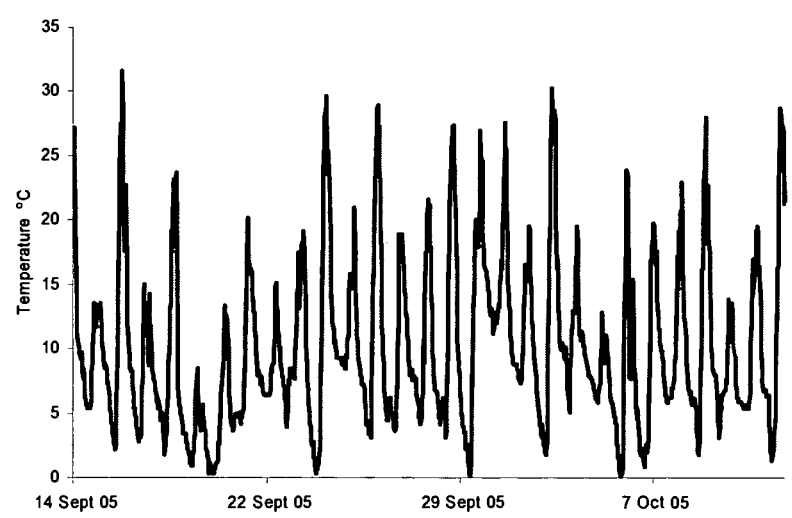
FIG. 11 shows Tunnel house temperature over the duration of the bioassay.

The average temperature within the tunnel house during the bioassay was 10° C. but ranged from 0 to 32° C. (see FIG. 11). This was higher than usual outside air temperatures for this time of year and may have affected larvae activity and plant growth.

Examples of Other Susceptible Invertebrate Species

Table 13 below summaries a list of various other invertebrate species, including the DBM and *Wiseana* spp tested for susceptibility to whole *Yersinia entomophaga* MH96 cells,

TABLE 13

Summary of the susceptibility of invertebrates to *Yersinia entomophaga* MH96.

| Insect | Class: Family | Developmental stage | Pathogenic? |
|---|---|---|---|
| Lepidoptera | | | |
| Diamondback moth *Plutella xylostella* | Lepidoptera: | 1st-4$^{th}$ instar larvae | yes |
| Porina *Wiseana copularis* | Lepidoptera: Heplidae | larvae | yes |
| Cotton bollworm *Helicoverpa amigera* | Lepidoptera: | larvae | yes |
| Greater wax moth *Galleria mellonella* | Lepidoptera: Galleriidae | larvae | yes |
| Painted apple moth *Teia anartoides* | Lepidoptera: Lymantriidae | larvae | yes |
| Greenheaded leafroller *Planotortrix notophaea* | Lepidoptera: Tortricidae | larvae | yes |
| Greenheaded leafroller *Planotortrix excessana* | Lepidoptera: Tortricidae | larvae | yes |
| Lightbrown apple moth *Epiphyas postvittana* | Lepidoptera: Tortricidae | larvae | yes |
| Brownheaded leafroller *Ctenoptusis* spp. | Lepidoptera: Tortricidae | larvae | yes |
| *Pieris rapae* white butterfly | Lepidoptera: ?Pieridae | larvae | yes |

TABLE 13-continued

Summary of the susceptibility of invertebrates to *Yersinia entomophaga* MH96.

| Insect | Class: Family | Developmental stage | Pathogenic? |
|---|---|---|---|
| Coleoptera | | | |
| New Zealand grass grub *Costelytra zealandica* | Coleoptera: Scarabaeidae | larvae | yes |
| Red headed cockchafer *Adoryphorus couloni* | Coleoptera: Scarabaeidae | larvae | yes |
| Tasmania grass grub *Acrossidius tasmaniae* | Coleoptera: Scarabaeidae | larvae | yes |
| Pericoptus truncatus Sand scarab | Coleoptera: Scarabaeidae | larvae | (yes) |
| Chafer beetles? *Odontria* sp. | Coleoptera: Scarabaeidae | larvae | (yes) |
| Bark beetle *Hylastes ater* | Coleoptera: Scolytidae | adults | partial |
| Black vine weevil *Otiorhynchus sulcatus* | Coleoptera: Curculionidae | larvae | yes |
| Clover root weevil (CRW) *Sitona lepidus* | Coleoptera: Curculionidae | adult | yes |
| Argentine stem weevil (ASW) *Listronotus bonariensis* | Coleoptera: Curculionidae | adult | adult- partial |
| Hymenoptera | | | |
| Darwin's ant *Doleromyrma darwiniana* | Hymenoptera: Formicidae | nest | yes |
| *Vespula vulgaris* Common wasps | Hymenoptera: Vespidae | larvae | yes |
| Orthoptera | | | |
| Locusts *Locusta migratoria* | Orthoptera: | neonates older instar | yes yes |
| Diptera | | | |
| root lesion nematode *Pratylenchus penetrans* | Nematoda | | slight |

It would be appreciated that the present invention provides a new biopesticide; or method for controlling insects which has a broad efficacy across a range of insects, and providing a new biopesticide in a range of different forms.

Aspects of the present invention have been described by way of example only and it should be appreciated that modifications and additions may be made thereto without departing from the scope thereof as defined in the appended claims.

REFERENCES

Aroonrat Teera-Arunsiri, Manop Suphantharika and Uthai Kentunuti. 2003. Preparation of Spray-Dried Wettable Powder Formulations of *Bacillus thuringiensis*-Based Biopesticides. Biological and Microbial Control. 96 (2): 292-299.

Bauce. E; Carisey, N.; Dupont, A.; van Frankenhuyzen, K (2004) *Bacillus thuringiensis* subsp. *kurstaki* Aerial Spray Prescriptions for Balsam Fir Stand Protection Against Spruce Budworm (Lepidoptera: Tortricidae) *Journal of Economic Entomology*, Volume 97, Number 5, October 2004, pp. 1624-1634(11) Entomological Society of America.

Bercovier, H. & Mollaret, H. H. (1984). Genus XIV. *Yersinia* Van Loghem 1944, 15$^{AL}$. In *Bergey's Manual of Systematic Bacteriology*, vol. 1, pp. 498-506. Edited by N. R. Krieg & J. G. Holt. Baltimore: Williams & Wilkins.

Burges, H. D. and Jones, K. A. (1998) Chapter 3 Formulation of bacteria, viruses and protozoa to control insects In Formulation of Microbial Biopesticides: Beneficial Microorganisms, Nematodes and Seed Treatments by H. Denis Burges: Kluwer Academic Publishers (October 1998) ISBN-10: 0412625202 ISBN-13: 978-0412625206.

Cashion, P., Holder-Franklin, M. A., McCully, J. & Franklin, M. (1977). A rapid method for the base ratio determination of bacterial DNA. *Anal Biochem* 81, 461-466.

Cathala G, Savourt J F, Mendez B, Karin M, Martial J M, Baxter J D, (1983). A method for isolation of intact translationally active ribonucleic acid. DNA 2, 239-335.

Chiou A. L. and Wu W. S. 2003. Formulation of *Bacillus amyloliquefaciens* B190 for Control of Lily Grey Mould (*Botrytis elliptica*). J. Phytopathology 151, 13-18.

De Ley, J., Cattoir, H. & Reynaerts, A. (1970). The quantitative measurement of DNA hybridization from renaturation rates. *Eur J Biochem* 12, 133-142.

Doonan, Shawn. Protein Purification Protocols, Humana Press, 1 Mar. 1996, Science, ISBN 0-89603-336-8

Pitcher, D. G.; Saunders, N. A; and Owen, R. J (1989) Rapid extraction of bacterial genomic DNA with guanidium thiocyanate. Letters in Applied Microbiology 8: 151-156.

Hofte, H., and H. R Whiteley. 1989. Insecticidial crystal proteins of *Bacillus thuringiensis*. Microbiol. Rev. 53: 242-255.

Huß; V. A. R., Festl, H. & Schleifer, K. H. (1983). Studies on the spectrometric determination of DNA hybridization from renaturation rates. *Syst Appl Microbiol* 4, 184-192.

Ibrahim, A., Liesack, W., Steigerwalt, A. G., Brenner, D. J., Stackebrandt, E. and Robins-Browne, R. M. (1997) A cluster of atypical *Yersinia* strains with a distinctive 16S rRNA signature. FEMS Microbiol. Lett. 146: 73-78.

Kado, C. I., and S.-T. Liu 1981. Rapid procedure for detection and isolation of large and small plasmids. J. Bacteriol. 145: 1365-1373.

Kotetishvili M, Kreger A, Wauters G, Morris J G Jr, Sulakvelidze A, Stine O C. (2005) Multilocus sequence typing for studying genetic relationships among *Yersinia* species. J Clin Microbiol. 43:2674-2684.

Lysenko. O (1985) Non-sporeforming bacteria pathogenic to insects:incidence and mechanisms. Ann Rev Microbiol 39:673-95.

Maa, Y.-F. and Prestrelski, S. J. (2000) Biopharmaceutical Powders: Particle Formation and Formulation Considerations. Current Pharmaceutical Biotechnology, 2000, 1, 283-302 283

Mesbah, M., Premachandran, U. & Whitman, W. B. (1989). Precise measurement of the G+C content of deoxyribonucleic acid by high-performance liquid chromatography. *Int J Syst Bacteriol* 39, 159-167.

O'Callaghan M. And Jackson T. A. Isolation and enumeration of *Serratia entomophila*—a bacterial pathogen of the New Zealand grass grub, *Costelytra zealandica*. J. Appl. Bacteriol., 1993, 75, 307-314.

Sambrook J and Russell D W (2001) Molecular Cloning: A Laboratory Manual. Third edition, Cold Spring Harbor Laboratory Press, Cold Spring Harbor, N.Y.

Scopes, R. K. (1993): Protein Purification: Principles and Practice) Springer-Verlag ISBN 0-387-94072-3

Steven E. Lindow and Trevor V. Suslow. 2003. Temporal Dynamics of the Biocontrol Agent Pseudomonas fluorescens Strain A506 in Flowers in Inoculated Pear Trees. Phytopathology 63 (6): 727-737.

What we claim is:

1. A non-naturally occurring freeze-dried and/or spray-dried composition comprising an isolated *Yersinia entomophaga* MH96 bacterium deposited at Leibniz Institute DSMZ-German Collection of Microorganisms and Cell Cultures GmbH (DSMZ) on 4 May 2006 and designated accession no. DSM 18238, a supernatant from a whole broth culture thereof, a cellular extract thereof, or a sonicated cell filtrate thereof, wherein said non-naturally occurring composition exhibits a biopesticide activity.

2. The composition of claim 1, wherein the composition is formulated with at least one biopolymer compound.

3. The composition of claim 2, wherein the at least one biopolymer compound is at least one type of gum compound.

4. The composition of claim 2, wherein the composition is formed into a prill or granule shape.

5. The composition of claim 2, wherein the composition is coated onto a substrate.

6. The composition of claim 5, wherein the substrate is a seed.

7. The composition of claim 1, wherein the composition is formulated with at least one biopolymer compound and at least one desiccating agent.

8. The composition of claim 7, wherein the at least one biopolymer compound is at least one type of gum compound and the at least one desiccating agent is at least one inert clay compound.

9. The composition of claim 7, wherein the formulated composition is a dough or granular material.

* * * * *

SEQUENCE LISTING

<160> NUMBER OF SEQ ID NOS: 9

<210> SEQ ID NO 1
<211> LENGTH: 18
<212> TYPE: DNA
<213> ORGANISM: Artificial Sequence
<220> FEATURE:
<223> OTHER INFORMATION: Primer

<400> SEQUENCE: 1
agagtttgat cctggctc                                                         18

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
tacggytacc ttgttacgac tt                                                    22

<210> SEQ ID NO 3
<211> LENGTH: 18
<212> TYPE: DNA
<213> ORGANISM: Artificial Sequence
<220> FEATURE:
<223> OTHER INFORMATION: Primer

<400> SEQUENCE: 3
gccgcggtaa tacggagg                                                         18

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
aggataaggg tttgcgctcc g                                                     21

<210> SEQ ID NO 5
<211> LENGTH: 36
<212> TYPE: DNA
<213> ORGANISM: Artificial Sequence
<220> FEATURE:
<223> OTHER INFORMATION: Primer

<400> SEQUENCE: 5
agtttgatca tggctcagtt accgcggctg ctggca                                     36

<210> SEQ ID NO 6
<211> LENGTH: 40
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 29, 32
<223> OTHER INFORMATION: r = G or A

<400> SEQUENCE: 6
cgattggtgg ctggaaaggc ttggtcatrg trttgaagcg                                 40

```
<210> SEQ ID NO 7
<211> LENGTH: 41
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 19, 28, 31
<223> OTHER INFORMATION: r = G or A
<220> FEATURE:
<221> NAME/KEY: misc_feature
<222> LOCATION: 13, 16, 37
<223> OTHER INFORMATION: y = T or C
<220> FEATURE:
<221> NAME/KEY: misc_feature
<222> LOCATION: 25
<223> OTHER INFORMATION: s = G or C

<400> SEQUENCE: 7
cggcggtttg cayggygtrg gcagsgtrcg rgtcatygcc g                41

<210> SEQ ID NO 8
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 16, 19, 29, 38, 41
<223> OTHER INFORMATION: r = G or A
<220> FEATURE:
<221> NAME/KEY: misc_feature
<222> LOCATION: 32, 44
<223> OTHER INFORMATION: y = T or C

<400> SEQUENCE: 8
gggccaaatt gaaaarcart tcggcgccra tyttcatrcg ratytggt           48

<210> SEQ ID NO 9
<211> LENGTH: 40
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 6
<223> OTHER INFORMATION: n = A,T,C or G

<400> SEQUENCE: 9
gacgtngtag aaggtatgya gcgccgccag ccagtttagc                    40
```